United States Patent
Xiang

(10) Patent No.: US 8,963,725 B2
(45) Date of Patent: Feb. 24, 2015

(54) TESTER AND TEST METHOD FOR SMOKE AMOUNT OF ELECTRONIC CIGARETTE

(71) Applicant: Zhiyong Xiang, Guangdong (CN)

(72) Inventor: Zhiyong Xiang, Guangdong (CN)

(73) Assignee: Kimree Hi-Tech Inc, Road Town, Tortola (VG)

( * ) Notice: Subject to any disclaimer, the term of this patent is extended or adjusted under 35 U.S.C. 154(b) by 8 days.

(21) Appl. No.: 13/900,294

(22) Filed: May 22, 2013

(65) Prior Publication Data

US 2014/0300480 A1    Oct. 9, 2014

Related U.S. Application Data

(63) Continuation of application No. PCT/CN2013/073742, filed on Apr. 3, 2013.

(51) Int. Cl.
*G08B 17/10*    (2006.01)
*G01N 21/53*    (2006.01)

(52) U.S. Cl.
CPC .............. *G08B 17/10* (2013.01); *G01N 21/534* (2013.01)
USPC .......................... 340/628; 340/652; 340/691.6

(58) Field of Classification Search
USPC ................. 340/630, 632, 628–629, 633–634, 340/636.17, 640–641, 652, 661, 691.6
See application file for complete search history.

(56) References Cited

U.S. PATENT DOCUMENTS

| | | | |
|---|---|---|---|
| 4,980,571 A | | 12/1990 | McRae et al. |
| 5,247,283 A | * | 9/1993 | Kobayashi et al. ............ 340/630 |
| 5,752,527 A | * | 5/1998 | Bowen et al. .................. 131/175 |
| 6,225,910 B1 | * | 5/2001 | Kadwell et al. ................ 340/630 |
| 8,159,359 B2 | * | 4/2012 | Forster ........................... 340/632 |
| 2005/0016550 A1 | * | 1/2005 | Katase ............................ 131/194 |
| 2009/0283104 A1 | * | 11/2009 | Hampl et al. .................. 131/334 |
| 2010/0305871 A1 | * | 12/2010 | Knox et al. ...................... 702/24 |
| 2014/0060556 A1 | * | 3/2014 | Liu ................................ 131/329 |

FOREIGN PATENT DOCUMENTS

| | | |
|---|---|---|
| CN | 2602372 Y | 2/2004 |
| CN | 101147053 A | 3/2008 |
| CN | 102096978 A | 6/2011 |
| CN | 201993877 U | 9/2011 |

OTHER PUBLICATIONS

International Search Report dated Dec. 26, 2013 for Application No. PCT/CN2013/073742.

* cited by examiner

*Primary Examiner* — Daniel Previl
(74) *Attorney, Agent, or Firm* — Tim Tingkang Xia, Esq.; Morris, Manning & Martin, LLP

(57) ABSTRACT

The invention relates to a tester and test method for smoke amount of electrical cigarette. The tester includes a collect device, a testing device, a control device as well as an input and output device. The input and output device is used to set test parameters, alarm and display a value of smoke amount and a test result whether qualified. The collect device, used to collect smoke, can precisely control a pumping smoke time and a pumping smoke capacity by introducing a step motor. The testing device, utilizing a light emitter and receiver, test a smoke amount. If the smoke amount tested is less than a predetermined smoke amount, an alarm system alarms by way of display and/or sound. The invention quantifies smoke amount of electronic cigarette, which can be adopted in the manufacture field of electronic cigarette to test smoke amount.

13 Claims, 4 Drawing Sheets

TESTER AND TEST METHOD FOR SMOKE AMOUNT OF ELECTRONIC CIGARETTE

CROSS-REFERENCE TO RELATED APPLICATIONS

This application is a continuation of International Patent Application No. PCT/CN2013/073742, with an international filing date of Apr. 3, 2013, designating the United States, now pending. The contents of these specifications are incorporated herein by reference.

BACKGROUND OF THE INVENTION

1. Field of the Invention

The invention relates to quality analysis tester, and more particularly to a tester and test method adopted in manufacture processing of electronic cigarettes.

2. Description of the Related Art

Electronics cigarettes, as smoking simulators, is one kind of electronic products, smokers inhale atomized smoke liquid to taste a flavor resembling that of a cigarette. To achieve the simulation effect, for one time inhalation of that, in the smoking time and smoking capacity in certain circumstances, the amount of smoke must reach a predetermined value, otherwise, a feeling of similar to that of a cigarette, and more the feeling of "enjoying", cannot be provided. Due to the differences of the components in the production process and the assembly process, resulting in some of the products cannot meet the above requirement. In order to ensure the quality of the electronic cigarettes, it is very necessary to examine the smoke amount of the finished electronic cigarettes. Currently, the test method for the smoke amount is still stuck in visual observation, after inhalation of the smoke by mouth or pumping the smoke into glass syringes, comparing it with a sample, and rough estimating whether the smoke amount is up to standard. The test method by visual observation is not reliable, the test result cannot be quantified, and cannot adapt to the modern large-scale production requirements.

SUMMARY OF THE INVENTION

It is therefore a primary object of the invention to provide a tester and test method, by which the test is in high efficiency and the test result is quantified, to test smoke amount of electronic cigarette. The above disadvantage is avoided.

The aforesaid object in accordance with the invention can be accomplished by providing a tester for smoke amount of electronic cigarette.

The tester includes a collect device, a testing device, a control device and an input/output device. The collect device is connected to a test port of an electronic cigarette through an air tube; the control device is electrically connected to the collect device, the testing device, and the input and output device.

The control device, according to a control parameter inputted, controls the collect device pumping a smoke amount from an electronic cigarette, then receives a test result from the test device, and analyzes the test result and gets a value of the pumped smoke amount, further compares the value of the pumped smoke amount with a value of minimum smoke amount, and controls the display and alarm according to the comparison result.

The collect device, used to collect a smoke amount from the electronic cigarette, comprises a step motor, a piston assembly and a transparent test chamber. The piston assembly is driven by the step motor, and the piston assembly inside the transparent test chamber moves along the axis direction of the transparent test chamber to pump smoke from electronic cigarettes into the transparent test chamber.

The testing device, used to test a transparency of the transparent test chamber, comprises a light emitter and a light receiver that are corresponding set in the sides or top and bottom of the transparent test chamber of the collect device, and the light form the light emitter to the light receiver can be infrared light, visible light or laser.

In one embodiment of the invention, the input and output device comprises a touch screen, a displayer and an alarm system. The touch screen is used to set control parameters and a minimum value of smoke amount, and shows a test result whether qualified. The displayer shows a value of pumped smoke amount. The alarm system alarms by way of display and/or sound.

In another embodiment of the invention, the input and output device comprises a touch screen and an alarm system. The touch screen is used to set control parameters and a minimum value of smoke amount, and displays a value of pumped smoke amount and a test result whether qualified. The alarm system alarms by way of display and/or sound.

The control device further comprises a control unit, an analysis unit and a processing unit, wherein, the control unit is used to receive control parameters inputted through the touch screen of the input/output device, controls the collect device pumping a smoke amount, and also control the testing device of which the light emitter emits a light and the light receiver collects the light;

the analysis unit receives alight intensity signal, i.e. a test result from the light receiver, the light intensity is determined by a transparency of the transparent test chamber, and the transparency is also determined by the value of pumped smoke amount in the transparent test chamber. Because the light intensity is corresponding to the value of pumped smoke amount, the analysis unit, analyzing the test result, gets a value of the pumped smoke amount, compares it with a value of minimum smoke amount, and generates a comparison result.

The processing unit outputs a signal of the value of the pumped smoke amount and signals of the comparison result whether qualified to the input/output device to display them, and sends an alarm signal to the input/output device to alarm if the comparison result is not qualified.

According to a tester for smoke amount of electronic cigarettes of the invention, the control device is configured as PLC controller or microcontroller.

The tester for smoke amount of electronic cigarettes of the invention, wherein the tester structure is an inner hollow cavity, the collect device, testing device and the control device are all fixedly disposed in the internal cavity, and the input/output device, a power supply switch, and the test port are respectively fixedly disposed in the cavity walls. The test port shape and opening size adopt outer periphery shape of the suction nozzle of the electronic cigarette.

A test method for smoke amount of electronic cigarettes is provided according to the invention, comprising following steps:

S1. Presetting control parameters and a value of minimum smoke amount;

S2. According the control parameters, pumping a smoke amount from an electronic cigarette;

S3. Testing the pumped smoke amount and receiving a test result, and analyzing the test result and getting a value of the pumped smoke amount, then comparing it with the value of the minimum smoke amount and generating a comparison result;

S4. Displaying the value of the pumped smoke amount and the comparison result whether qualified, and alarming if the comparison result is not qualified.

The test method for smoke amount of electronic cigarettes according to the invention, the control parameters includes a smoking time and a smoking capacity, the value of minimum smoke amount is defined as a value of qualified minimum smoke amount in the smoking time and smoking capacity in certain circumstances.

The test method for smoke amount of electronic cigarettes according to the invention, the step S2 further comprising in:

S21. A control unit of a control device controls a step motor of a collect device running according to the control parameters.

S22. the step motor drives a piston assembly inside a transparent test chamber of the collect device, the piston assembly moves along the axis direction of the transparent test chamber to pump a smoke amount from an electronic into the transparent test chamber;

The test method for smoke amount of electronic cigarettes according to the invention, the step S3 further comprising in:

S31. the control unit of the control device controls a testing device of which a light emitter emits a light and a light receiver collecting the light. A test result from the light receiver is sent to an analysis unit of the control device.

S32. the analysis unit analyzes the test result, and gets a value of the pumped smoke amount, then compares it with the value of the minimum smoke amount to generate a comparison result.

The test method for smoke amount of electronic cigarettes according to the invention, the step S4 further comprising in: a processing unit of the control device outputs a signal of the value of the pumped smoke amount to a touch screen or a displayer of the input/output device to display it.

According the comparison result, the processing unit sends a signal to control the touch screen showing "PASS" if the value of pumped smoke amount is greater than the value of minimum smoke amount, otherwise sends signals to control the touch screen showing "FAIL" and also triggers an alarm system in the input/output device.

According to the invention, a step motor introduced into the collect device and precisely controls both pumping smoke time and pumping smoke capacity according to the setting control parameters. A touch screen is used to set control parameters and display comparison result, makes the operation simpler. A light emitter and light receiver adopted make the test for smoke amount can be quantified. An automatic alarm system alarms by way of display and sound when a pumped smoke amount is less than a minimum smoke amount.

BRIEF DESCRIPTION OF DRAWINGS

The invention can be more fully understood by reading the subsequent detailed description and examples with reference made to the accompanying drawings, wherein.

DETAILED DESCRIPTION OF THE INVENTION

The following description is of the best contemplated of carrying out the invention. The description is made for the purpose of illustrating the general principle of the invention and should not be taken in a limiting sense. The scope of the invention is best determined by reference to the appended claims.

Embodiment 1

Figure 1:
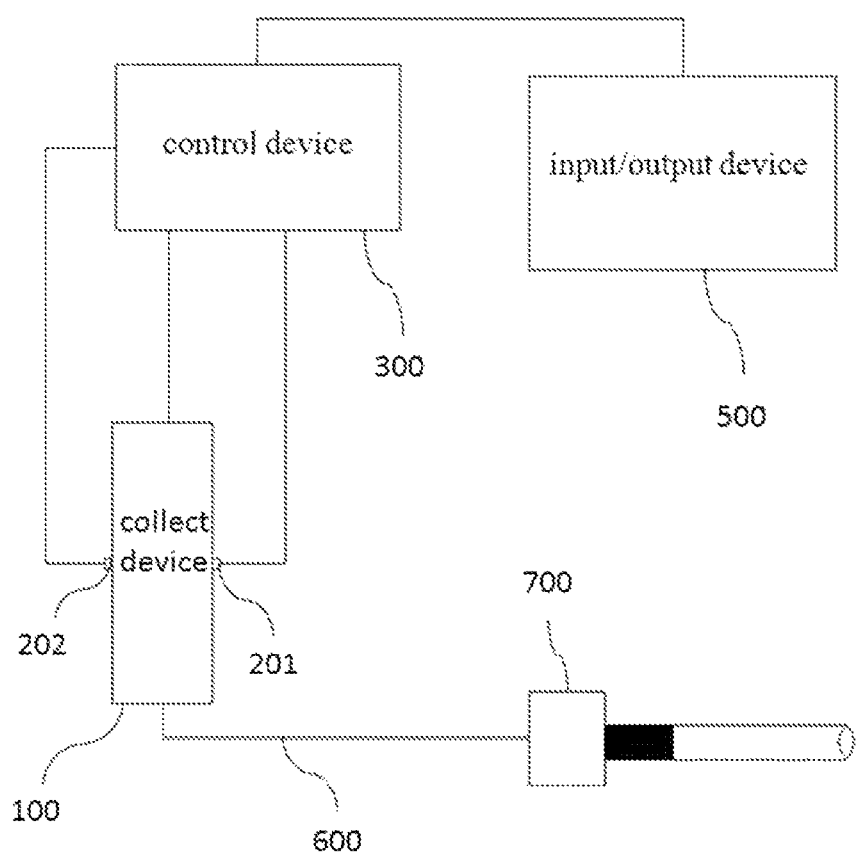
FIG. 1 is a schematic diagram of a tester for smoke amount of electronics of the invention.

Referring to FIG. 1, a tester for smoke amount of electronic cigarettes includes a collect device 100 used to collect a smoke amount, a testing device used to a test a transparency of transparent test chamber, a control device 300 and an input/output device 500. The collect device 100 is connected to a test port 700 for pumping a smoke amount from an electronic cigarette through an air tube 600. The testing device comprises a light emitter 201 and light receiver 202 that are corresponding set in the sides or top and bottom of a transparent test chamber of the collecting device 100. The control device 300 is electrically connected to the collect device 100, the testing device, the input/output device 500 and an alarm system 503.

The control device 300, according to control parameters inputted, controls the collect device 100 pumping a smoke amount from an electronic cigarette, then receives a test result from the testing device, and analyzes the test result and gets a value of pumped smoke amount, further compares it with the value of minimum smoke amount, and sends signals to the input/output device 500 according to a comparison result. The value of the minimum smoke amount is that for one time inhalation of that, in the smoking time and smoking capacity in certain circumstances, the amount of smoke must reach a predetermined value, so a feeling of similar to that of a cigarette, and more the feeling of "enjoying" can be provided. When the value of the minimum smoke amount of an electronic cigarette cannot be reached, there may be quality problem in the electronic cigarette, the cause has to be checked out from its atomizer, casing, inhalation hole etc.

The light form the light emitter 201 to the light receiver 202 in the testing device can be infrared light, visible light or laser. Their working principles are the same. The light with certain intensity from the light emitter 201 goes through a transparent test chamber 103, the light intensity may be attenuated according to a transparency of the transparent test chamber 103, to the light receiver 202. The transparency is determined by a value of pumped smoke amount in the transparent test chamber 103. The light intensity received by the light receiver 202 is finally determined by the pumped smoke amount in the transparent test chamber 103. The value of the light intensity is 1 when there is no any smoke in the transparent test chamber 103, or is 0.1 when there is saturated smoke in the transparent test chamber 103. The control device 300 can analyze and get a value of a pumped smoke amount according to a signal of light intensity from the light receiver 202.

Figure 2:
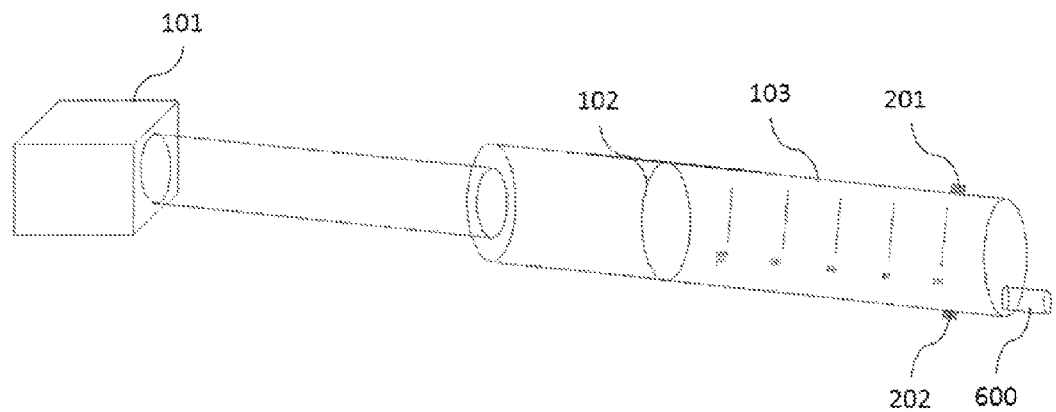
FIG. 2 is a schematic diagram of a collect device of the invention.

Referring FIG. 2, the collect device comprises a step motor 101, a piston assembly 102 and the transparent test chamber 103, wherein the step motor drives a piston assembly inside the transparent test chamber 103, the piston assembly moves along the axis direction of the transparent test chamber 103 to pump a smoke amount from an electronic cigarette into the transparent test chamber 103. The control device 300 controls the step motor 103 pumping a smoke amount through a precise smoking time and smoking capacity.

The control device 300 is configured as a generic PLC controller, comprises a control unit, an analysis unit and a processing unit, wherein The control unit of the control device 300, being used to receive control parameters in putted through the touch screen of the input/output device 500, controls the collect device 100 pumping a smoke amount, and also control the testing device of which the light emitter 201 emits a light and the light receiver 202 collects the light; The analysis unit receives a light intensity signal i.e. a test result from the light receiver 202, analyzes the test result and gets a value of the pumped smoke amount, further compares it with a predetermined minimum value of the smoke amount and generates a comparison result. The processing unit of the control device 300 outputs a signal of the value of the pumped smoke amount and a signal of the comparison result whether qualified to the input/output device 500 to display them, and sends an alarm signal to the input/output device 500 to alarm if the comparison result is not qualified.

The input/output device 500 comprises a touch screen 501, a displayer 502 and an alarm system 503. The touch screen 501 is used to set control parameters and a value of minimum smoke amount, and shows a comparison result whether qualified. The displayer 502 shows a value of pumped smoke amount. The alarm system 503 alarms by way of display and/or sound. The alarm system can be an alarm light with one of red, yellow or any other easily lead to note the color, and/or be a speaker.

Figure 3:
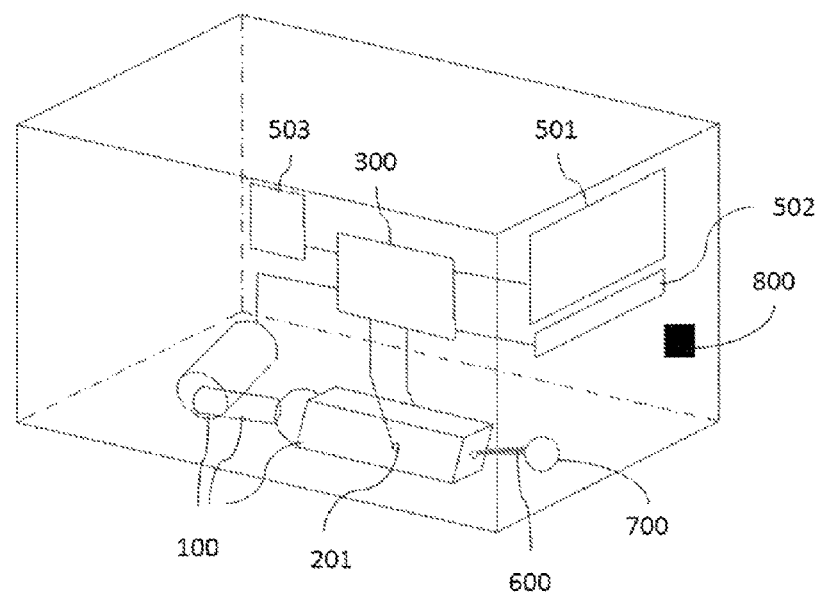
FIG. 3 is a first example of a structure of the tester for smoke amount of electronic cigarette of the invention.

Referring FIG. 3, a tester for smoke amount of electronic cigarettes, wherein the test structure is an inner hollow cavity. The collect device 100, the testing device and the control device 300 are all fixedly disposed in the internal cavity. The testing device comprises the light emitter 201 and the light receiver 202 (not shown). The input/output device 500, comprising the touch screen 501, the displayer 502 and the alarm system 503, the power switch 800 and the test port 700 are respectively fixedly disposed in the cavity walls. The power switch 800 is used to turn on/off an external power supply. The test port 700 shape and opening size adopt outer periphery shape of the suction nozzle of the electronic cigarette.

Figure 5:
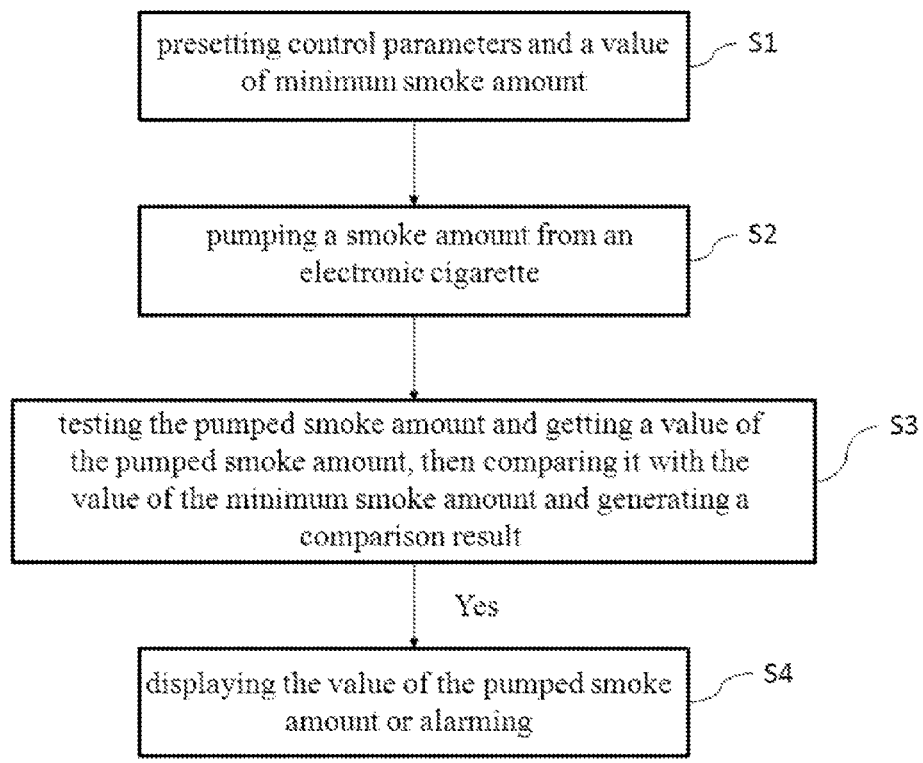
FIG. 5 is a flowchart of a test method for smoke amount of electronic cigarettes.

Referring FIG. 5, the embodiment of a test method for smoke amount of electronic cigarettes is further illustrated; the work process includes the following steps:

S1. Preset control parameters and a value of minimum smoke amount by operator via the input/output device 500. The control parameters comprise a smoking time and smoking capacity, and the value of minimum smoke amount is that in the smoking time and smoking capacity in certain circumstances, the smoke amount inhaled from an electronic cigarette must reach a predetermined value;

S2. The control unit of the control device 300 receives the control parameters and the value of minimum smoke amount, and precisely controls the step motor of the collect device 100 running according the control parameters, the step motor drives a piston assembly inside a transparent test chamber of the collect device 100, the piston assembly moves along the axis direction of the transparent test chamber to pump a smoke amount from an electronic cigarette into the transparent test chamber. The control device controls the step motor pumping a smoke amount according to the precise smoking time and smoking capacity.

S3. The control unit of the control device 300 controls the testing device of which the light emitter 201 emits a light and the light receiver 202 collects the light. The analysis unit of the control device 300 receives a light intensity signal i.e. a test result from the light receiver 202, the value of light intensity is in the range between 0.1~1 and determined by the value of the pumped smoke amount in the transparent test chamber. The analysis unit analyzes the test result, gets a value of the pumped smoke amount, compares it with the value of minimum smoke amount, and generates a comparison result. According to the comparison result, if the value of pumped smoke amount is less than the minimum value of smoke amount, go to next step, otherwise jump to S5.

S4. The processing unit of the control device 300 sends an alarm signal to the alarm system 503 of the input/output device 500 to alarm, and outputs a signal of the value of the pumped smoke amount and signal of "FAIL" to the input/output device 500 to display them.

S5. The processing unit of the control device 300 outputs a signal of the value of the pumped smoke amount and signal of "PASS" to the input/output device 500 to display them.

Were combined with specific types of light, control parameters and a minimum value of smoke amount, the tester of invention is illustrated as following:

The testing device consists of the laser emitter 201 and the laser receiver 202. Setting a smoking time as 1 second, a smoking capacity as 60 ml and a value of minimum smoke amount as 2 mg according to the smoking time as 1 second and smoking capacity as 60 ml, alight intensity received by the laser receiver 202 shall be 0.8 corresponding to the 2 mg of minimum smoke amount. The collecting device 100 controlled by the control device 300 pumps a smoke amount from an electronic cigarette according to the 1's for the smoking time and 60 ml for the smoking capacity. Then the testing device begins to test. If the light intensity received by the laser receiver 202 is 0.85, the analysis unit of the control device 300 can analyzes it and gets 1.5 mg as the value of the pumped smoke amount, and compares the value of 1.5 mg of the pumped smoke amount with the value of 2.0 mg of minimum smoke amount and generates a comparison result.

According to the value of 1.5 mg and the comparison result, the control device 300 outputs a signal of the value of 1.5 mg to the displayer 502 to display it and outputs a signal of "FAIL" to the touch screen 501 to display it, also sends an alarm signal to the alarm system 503 to alarm. To adopt other kinds of light, a proportion relation of the light intensive corresponding to the smoke amount may change, but cannot change the working principle of the light intensity is inversely proportional to the smoke amount. They are not needed to show one by one.

Embodiment 2

Figure 4:
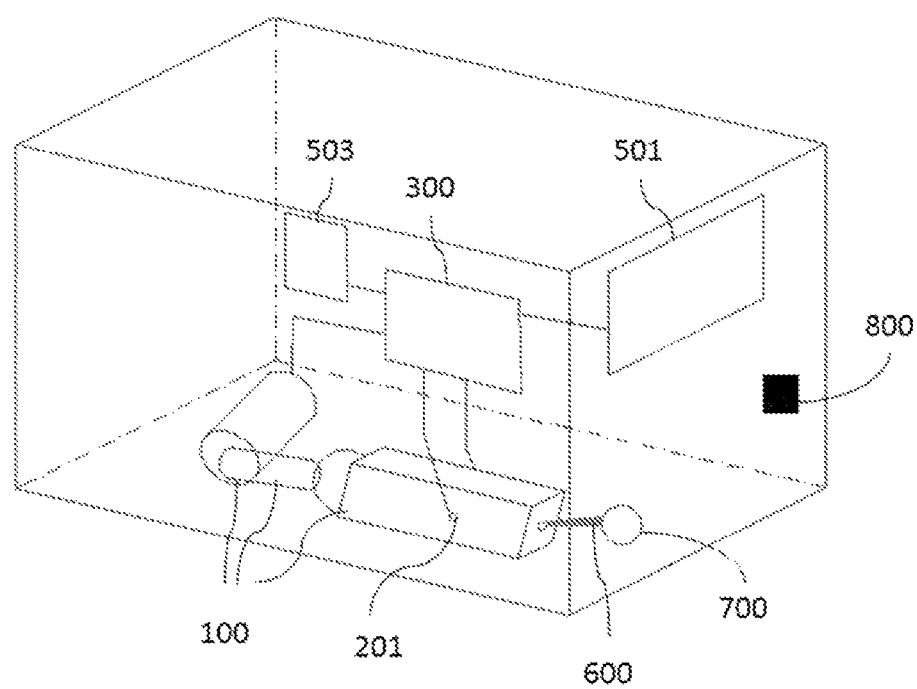
FIG. 4 is a second example of a structure of the tester for smoke amount of electronic cigarette of the invention.

Referring FIG. 4, a tester for smoke amount of electronic cigarettes, its structure is basically same as the embodiment 1, wherein the control device 300 is configured as a generic microcontroller, the input/output 500, omitting a displayer, comprises the touch screen 501 and the alarm system 503. The touch screen is used to set control parameters and a value of minimum smoke amount, and display a value of pumped smoke amount and a comparison result whether qualified. A microprocessor as a control device of a tester for smoke amount of electronic cigarettes, the entire tester reflect a faster, at the same time can enhance the scalability of this tester, such as adding a storage device can be tested accordingly storage and can export data, add data analysis and processing system that can come to the rate of qualified products and results. Omit the displayer so that the entire tester more concise and easy to operate.

While the invention has been described by way of example and in terms of preferred embodiment, it is to be understood that the invention is not limited thereto. Those who are skilled in this technology can still make various alteration and modification without departing from the scope and spirit of this invention. Therefore, the scope of the present invention shall be defined and protected by the following claims and equivalents.

What is claimed is:

1. A tester for smoke amount of electronic cigarette, comprising a collect device, a testing device, a control device, and an input and output device,
   wherein the collect device is connected to a test port of an electronic cigarette through an air tube; the control device is electrically connected to the collect device, the testing device, and the input and output device;
   wherein the control device, according to control parameters inputted, controls the collect device to pump a smoke amount from an electronic cigarette, receives a test result from the testing device, analyzes the test result and obtains a value of the pumped smoke amount, further compares the value of the pumped smoke amount with a value of minimum smoke amount, and controls display and/or an alarm according to a comparison result;
   wherein the collect device is used to collect a smoke amount from an electronic cigarette; and
   wherein the testing device, used to test a transparency of a transparent test chamber of the collect device, comprises a light emitter and a light receiver, and the light emitter and the light receiver are correspondingly set in sides or top and bottom of the transparent test chamber of the collect device.

2. The tester for smoke amount of claim 1, wherein the collect device further comprises a step motor, a piston assembly and the transparent test chamber; the piston assembly is driven by the step motor, and the piston assembly is inside the transparent test chamber and moves along an axis direction of the transparent test chamber to pump smoke from electronic cigarettes into the transparent test chamber.

3. The tester for smoke amount of claim 1, wherein light from the light emitter to the light receiver can be infrared light, visible light or laser.

4. The tester for smoke amount of claim 1, wherein the input and output device further comprises a touch screen, a displayer and an alarm system; the touch screen is used to set control parameters and a value of minimum smoke amount, and shows whether a comparison result is qualified; the displayer shows a value of pumped smoke amount; the alarm system alarms by displaying and/or sounding.

5. The tester for smoke amount of claim 4, wherein the control device further comprises a control unit, an analysis unit and a processing unit,
   wherein the control unit receives control parameters inputted through the touch screen, controls the collect device to pump a smoke amount, and simultaneously controls the light emitter to emit light and the light receiver to collect the light;
   wherein the analysis unit receives a light intensity signal as the test result from the light receiver to analyze the test result and to obtain a value of the pumped smoke amount, compares the value of the pumped smoke amount with a value of minimum smoke amount and generates a comparison result; and
   wherein the processing unit outputs a first signal of the value of the pumped smoke amount and a second signal of whether the comparison result is qualified to the input and output device so as to display the first and second signals, and/or sends an alarm signal to the input and output device so that the input and output device alarms if the comparison result is not qualified.

6. The tester for smoke amount of claim 1, wherein the input and output device further comprises a touch screen and an alarm system, the touch screen is used to set control parameters and a value of minimum smoke amount, and displays a value of pumped smoke amount and whether a comparison result is qualified; the alarm system alarms by displaying and/or sounding.

7. The tester for smoke amount of claim 1, wherein the control device is configured as PLC controller or microcontroller.

8. The tester for smoke amount of claim 7, wherein a structure of the tester is an inner hollow cavity,
   wherein the collect device, the testing device and the control device are all fixedly disposed inside the cavity;
   wherein the input and output device, a power supply switch, and the test port are respectively fixedly disposed on walls of the cavity; and
   wherein a size and a shape of an opening of the test port fit a size and a shape of an outer periphery of a suction nozzle of the electronic cigarette.

9. A test method for smoke amount of electronic cigarettes, comprising following steps:
   S1: presetting control parameters and a value of minimum smoke amount;
   S2: according to the control parameters, pumping a smoke amount from an electronic cigarette;
   S3: testing the pumped smoke amount and receiving a test result, and analyzing the test result and obtaining a value of the pumped smoke amount, then comparing the value of the pumped smoke amount with the value of minimum smoke amount and generating a comparison result; and
   S4: displaying the value of the pumped smoke amount and whether the comparison result is qualified, and alarming if the comparison result is not qualified.

10. The test method of claim 9, wherein the control parameters comprise a smoking time and a smoking capacity, and the value of minimum smoke amount is a value of minimum smoke amount satisfying a qualifying condition within the smoking time and the smoking capacity.

11. The test method of claim 9, wherein the step S2 further comprises following steps:
    S21: a control unit of a control device controls a step motor of a collect device to run according to the control parameters; and
    S22: the step motor drives a piston assembly inside a transparent test chamber of the collect device, and the piston assembly moves along an axis direction of the transparent test chamber to pump a smoke amount into the transparent test chamber.

12. The test method of claim 9, wherein the step S3 further comprises following steps:
    S31: a control unit of a control device controls a light emitter in a testing device to emit light and a light receiver in the testing device to collect the light, and controls a test result signal to be sent from the light receiver to an analysis unit of the control device; and
    S32: the analysis unit analyzes the test result and obtains a value of the pumped smoke amount, then compares the value of the pumped smoke amount with the value of the minimum smoke amount to generate a comparison result.

13. The test method of claim 9, wherein the step S4 further comprises:
- a processing unit of a control device outputs a signal of the value of the pumped smoke amount and a signal of whether the comparison result is qualified to an input and output device;
- a touch screen or a displayer of the input and output device displays the value of the pumped smoke amount, and displays a comparison result as qualified when the value of the pumped smoke amount is greater than the value of the minimum smoke amount, or displays a comparison result as not qualified when the value of the pumped smoke amount is equal to or smaller than the value of the minimum smoke amount; and
- the processing unit triggers an alarm system of the input and output device when a comparison result is not qualified.

* * * * *